(12) United States Patent
Manickam

(10) Patent No.: US 8,221,802 B2
(45) Date of Patent: *Jul. 17, 2012

(54) ANTIPYROTIC FORMULATION FOR THE TREATMENT OF EPIDERMAL BURNS

(75) Inventor: Sai S. Manickam, Lutz, FL (US)

(73) Assignee: The Akshay Wellness Group, Inc., Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/098,795

(22) Filed: May 2, 2011

(65) Prior Publication Data

US 2011/0206774 A1    Aug. 25, 2011

Related U.S. Application Data

(63) Continuation of application No. 12/137,026, filed on Jun. 11, 2008, now Pat. No. 7,959,955.

(60) Provisional application No. 60/944,317, filed on Jun. 15, 2007.

(51) Int. Cl.
*A61K 36/00* (2006.01)
*A61K 36/886* (2006.01)
*A61K 31/74* (2006.01)
*A61K 36/28* (2006.01)

(52) U.S. Cl. ...................... 424/725; 424/78.06; 424/737; 424/744; 514/846; 514/969; 514/944; 514/937

(58) Field of Classification Search .................. None
See application file for complete search history.

(56) References Cited

U.S. PATENT DOCUMENTS

| 4,163,049 A | 7/1979 | Aubin |
| 6,306,443 B1 | 10/2001 | Brovelli et al. |
| 6,309,664 B1 | 10/2001 | Mathur et al. |
| 7,288,622 B1 | 10/2007 | Jaynes et al. |
| 2006/0177526 A1 | 8/2006 | Rittinghausen et al. |
| 2007/0275108 A1 | 11/2007 | Geesamen |

FOREIGN PATENT DOCUMENTS

AU    2006200131 A1    7/2006

OTHER PUBLICATIONS

*Lytta vesicatoria* synonyms at Nomen. At—animal and plants, Dictionary of common names, pp. 1-2, accessed on Mar. 4, 2009.

Takami et al., Healing effect of superoxide dismutase (SOD) ointment on open wounds and burn ulcers in rats, Nippon Yakuzaishi Kyokai, 1993: 53 (3): 185-190.

*Primary Examiner* — Qiuwen Mi

(74) *Attorney, Agent, or Firm* — Ward and Smith, P.A.

(57) ABSTRACT

A unique, synergistic formulation for the treatment of first-degree skin burns is provided for topical use and alleviates the full spectrum of symptoms and concerns associated with epidermal burns, including pain, blistering, redness, swelling, compromised skin integrity, risk of infection and scarring. The formulation contains natural homeopathic extracts combined with a pharmaceutically acceptable carrier suitable for topical administration. The formulation may include three or more of the following homeopathic extracts: *Cantharis Vesicatoria, Echinacea Angustifolia, Calendula Officinalis* and *Hypericum Perforatum.*

17 Claims, No Drawings

ANTIPYROTIC FORMULATION FOR THE TREATMENT OF EPIDERMAL BURNS

CROSS REFERENCE TO RELATED APPLICATIONS

This application is a continuation application of U.S. patent application Ser. No. 12/137,026 (now issued as U.S. Pat. No. 7,959,955), filed Jun. 11, 2008, which claims priority to U.S. Provisional Patent Application Ser. No. 60/944,317 filed Jun. 15, 2007. Applicant expressly claims priority to the filing date of the parent U.S. patent application Ser. No. 12/137,026 and the U.S. Provisional Application Ser. No. 60/944,317, the disclosures of both being specifically incorporated by reference herein.

BACKGROUND OF THE INVENTION

1. Field of the Invention

This invention is related to formulations and methods for treating burns. More particularly, the invention relates to formulations and methods for treating, through topical application, first- and second-degree burns and sunburns from a broad range of causes including thermal, electrical, chemical and radiation burns, and the entire range of symptoms thereof, including pain, redness, skin irritation, blistering, peeling and scarring.

2. Prior Art Discussion

Skin burns are typically classified in three levels of severity, namely, first-degree, second-degree and third-degree burns. Burns which affect only the outermost layers of skin (epithelium), causing pain, swelling, redness and moderate scarring are classified as first-degree burns. First-degree burns are considered to be self-limiting, i.e., the symptoms are expected to disappear in due course without the necessity for therapeutic intervention or medical care. As such, most of the conventional treatment options are limited to lessening or masking pain and/or preventing infection.

Second-degree burns are generally more severe and manifest as erythema with superficial blistering of the skin. They affect the epithelium and some of the underlying dermal layer of the skin extending, in the most severe cases, to the soft tissue. They cause pain, swelling, blistering, peeling and redness, and can often result in permanent scars. Second degree burns can involve more or less pain depending on nerve involvement. The symptoms of minor second-degree burns, other than scarring, usually disappear in due course without therapeutic intervention. However, because the distinction between minor and severe second-degree burns is subjective and dependent on the specific pain threshold and circumstances of each person, second-degree burns are generally deemed not to be self-limiting. Hence, people who suffer second-degree burns either assume them to be first-degree burns and do not seek treatment, or seek outpatient medical treatment for them. Common treatment options for second-degree burns include antibacterial ointments, cold compresses, bandages, blister pads, and home remedies such as aloe vera gel. Some medical professionals may prescribe Silvadeen®, a silver-based antimicrobial ointment.

Third-degree burns affect the epidermis, endodermis, and extend into the deeper tissues of the skin, causing severe pain, shock, nerve damage resulting in numbness and permanent disfigurement of affected areas. More particularly, with third degree burns most of the skin is lost with damage to underlying ligaments, tendons and muscles. Burn victims will exhibit charring of the skin, and sometimes hard eschars will be present. These burns are often considered painless because nerve endings have been destroyed in the burned area. If the affected area is significantly large, such burns may be fatal. Third-degree burns require emergency medical care and involve significant recovery.

Sunburn is not typically classified in the same way as thermal burns, although they share the same symptoms. Sunburns are caused by overexposure of the skin to the sun, or to sun-equivalent sources such as tanning beds, and are more specifically caused by exposure to ultraviolet (UV) radiation. Sunburns are characterized by pain, soreness, redness, irritation blistering and peeling. Prolonged and severe exposure to the sun can result in shock, overheating, damage to internal organs and even death. This level of severity is not considered to be within the scope of the definition of "minor sunburns" for the purposes of this application.

Burns can be caused by dry heat (fire), wet heat (steam, hot liquids), radiation, heated objects, electricity and chemicals. Thermal burns and sunburns are the most common type of burns. Thermal burns can occur when hot metals, scalding liquids, steam or flames come in contact with skin through incidences such as fires, accidents, electrical malfunctions or unsafe or accidental handling of hot objects.

First-degree burns, second-degree burns and minor sunburns are together defined as epidermal burns for the purposes of this application.

The immediacy of treatment following an epidermal burn is an important factor in the effectiveness of the treatment, especially with respect to preventing infection and scarring. Other common "home remedies" for epidermal burns include the running of cold water on the affected area, and/or the application of ice, butter, a cold compress or applying other cooling substances to the affected area.

Those who experience epidermal burns may also treat the burns with over-the-counter products, including anti-bacterial ointments or analgesic ointments and creams. However, these conventional treatment options have a number of limitations. Although water may cool the affected area, the relief is temporary and can increase the risk of infection. Butter is believed to trap heat on the burn site and increase the risk of infection. Cold compresses and gauze pads isolate the affected area from fresh air, which can hinder healing. Analgesics and petrolatum-based ointments either serve only to relieve pain in the former case, or merely create an occlusive barrier on the skin without directly treating the burn. There also exist a limited number of burn care kits, which typically require several complicated steps for effective use. As noted above, conventional options for the treatment of epidermal burns are neither comprehensive nor broadly effective; few single products available today purport to address the full range of symptoms of epidermal burns.

The prevalence of epidermal burns and the inadequacy of current treatment options has been substantiated by market research. A recent survey revealed that 70% of consumers surveyed suffer minor household burns on a regular basis from activities such as cooking, grilling, working in the garage or styling hair. However, 3 out of every 4 consumers surveyed stated they do not currently have an effective solution to care for their burns.

The present invention was specially formulated to address the deficiencies of conventional burn treatments in a single therapeutic treatment. The present invention has been found to have remarkable results in the treatment of epidermal burns, including a synergistic therapeutic effect compared to the therapeutic scope of its individual components.

BRIEF SUMMARY OF THE INVENTION

The active agents contained in the subject invention are natural homeopathic extracts. Homeopathy is a branch of alternative medicine based on the utilization of specially prepared, extreme dilutions of natural substances to trigger a healing response in the body. The word "homeopathy" derives from the Greek words homoios meaning "similar" and pathos meaning "suffering".

One aspect the invention involves an antipyrotic formulation that is therapeutically effective for treating epidermal burns. This formulation includes a mixture of at least three of the following extracts: *Cantharis Vesicatoria, Calendula Officinalis, Echinacea Angustifolia* and *Hypericum Perforatum*. At least three of these ingredients, at specific potencies and amounts best suited for the specific degree and type of burn to be treated, are compounded with a pharmaceutically acceptable carrier for topical application.

While reference may be made herein to specific carriers such as a cream emulsion, alcohol solvent, or petrolatum-based ointment, it will be readily apparent to those of ordinary skill that any number of alternative carrier formulations may be employed so long as they are pharmaceutically acceptable and suitable for topical administration. Still further, the formulation can alternatively be deployed in a spray aerosol or pump dispensing liquid container. In yet another alternative form, the formulation can be carried on a bandage, or in other forms known to or readily ascertainable by those of ordinary skill.

The most preferred and generally applicable combination is comprised of *Cantharis Vesicatoria, Calendula Officinalis* and *Echinacea Angustifolia*. In this case, the total amount of the homeopathic extracts relative to the aggregate composition would be less than approximately ten percent (10%). The composition may be combined with a petrolatum carrier as an ointment or delivered in a cream emulsion.

In another aspect, the invention involves a method of treating burns which involves administering to the burned area of a patient's skin a formulation as previously described.

DETAILED DESCRIPTION OF THE INVENTION

Homeopathy was founded in the late 18th century in Germany by a physician named Dr. Samuel Hahnemann. Hahnemann discovered that by ingesting extract of cinchona, which contains quinine that is used to cure malaria, he was able to develop the well-known symptoms of malaria. This was the basis of the first law, known as the Law of Similars, or "like cures like." This law states that "a substance that produces a certain set of symptoms in a healthy person has the power to cure a sick person manifesting those same symptoms."

While most allopathic drugs act by blocking biochemical pathways, homeopathy is believed to use a more subtle energy system that triggers a healing response in the body, with no known side effects or deaths in its entire 200+ year history. Homeopathic medicines are manufactured and labeled under specifications recognized by the United States Food and Drug Administration. After herbal medicine, homeopathy is the second most widely used health care system in the world. Over a half a billion people around the world use homeopathy as alternative or primary care for illnesses. Homeopathy is highly respected in many parts of the world, and is part of the national health care system in the United Kingdom. The World Health Organization has cited homeopathy as one of the systems of traditional medicine that should be integrated worldwide to provide adequate global health care.

Homeopathic remedies, and those of the invention, are prepared through a process of dilution and potentization. The second law of Homeopathy, or the Law of Infinitesimals, states that diluting a remedy makes it more powerful.

Hahnemann developed certain dilution and other techniques to prepare homeopathic remedies at specific concentrations and potencies, techniques which are still used today to manufacture homeopathic remedies. First, the homeopathic tincture, once extracted from its natural source, is combined with pure alcohol at a ratio of alcohol to tincture of 99:1. The combination is then mixed by banging the container on a hard surface, a process called "succession," a step homeopathic practitioners believe is essential to making an effective remedy.

The initial step of dilution results in a remedy with a dilution of one part in 100, also noted by "c" (centesimal) or by the term "2x". The dilution is then repeated, always by adding one part of tincture to 99 parts alcohol, and succussing at each step. Such a process carried out six times would lead to a potency of 12x (also known as 6c), and so forth.

The homeopathic ingredients used in the various embodiments of the invention are discussed in greater detail as follows.

*Cantharis Vesicatoria* is a homeopathic ingredient obtained from the insect *Lytta vesicatoria*, more commonly known as Spanish fly or blister beetle. This beetle lives on honeysuckle and olive trees in western Asia and southern Europe. It is bright green and about 0.5 in (1.3 cm) in length.

The Spanish fly produces a toxic substance called cantharidin. Cantharidin is a strong poison that primarily affects the urinary tract and causes burning pain and vomiting. Cantharidin is caustic and causes skin blistering. Since homeopathy is based on the Law of Similars, this homeopathic remedy is used for illnesses that have burning pain as a symptom.

*Cantharis* is also used to treat burns or skin conditions that resemble burns. It is used for sunburn, blisters, skin eruptions and insect bites. Symptoms associated with burns for which *cantharis* is indicated include blister formation, searing pain and relief upon application of a cold compress. This remedy has been used to relieve the pain associated even with second or third degree burns. *Cantharis* is indicated for blisters that are burning and itching and feel better upon application of a cold compress.

A second optional ingredient in the formulation of the invention is *Calendula Officinalis*. This homeopathic ingredient is also known as garden marigold. It is a member of the asteraceae family. Other members of this plant family include daisies, arnica, chamomile and yarrow. *Calendula* is native to Asia and southern and central Europe. It is cultivated throughout the world and valued for its culinary and medicinal uses.

During the Civil War, *calendula* was used to stop the blood flow from battle wounds. *Calendula* blossom preparations continue to be valued as an antiseptic for external application to scrapes, burns, cuts or wounds. Local application, in the form of a plant poultice or an infusion soaked in a cloth and applied to a wound, is deemed to be a time-tested and effective healing remedy. The flowers have antispasmodic, antimicrobial and antiviral properties. They improve the circulation of the blood and the lymphatic fluids and aid in elimination of toxins from the body. The juice from the fresh flowers or stem is said to help remove warts and help heal mucous membranes and skin.

A third optional ingredient in the formulation of the invention is *Echinacea Angustifolia*. This homeopathic ingredient, also known as the purple coneflower, is a perennial herb native to the North American prairie, abundant in the Midwest, and cultivated widely in ornamental and medicinal gardens.

*Echinacea* is most often used to boost the immune system and fight infection. Research has shown that Echinacea increases production of interferon in the body. It is antiseptic and antimicrobial, with properties that act to increase the number of white blood cells available to destroy bacteria and slow the spread of infection. As a depurative, the herbal extract cleanses and purifies the bloodstream, and has been used effectively to treat boils. *Echinacea* is vulnerary, promoting wound healing through the action of a chemical substance in the root known as caffeic acid glycoside. As an alternative and an immunomodulator, *Echinacea* acts gradually to promote beneficial change in the entire system.

A fourth optional ingredient in the formulation of the invention is *Hypericum Perforatum*, commonly known as St. John's Wort. It is commonly grown in temperate and subtropical regions of North America, Europe, Asia Minor, Russia, India and China.

*Hypericum* is a perennial plant with extensive, creeping rhizomes. Its stems are erect, branched in the upper section, and can grow to 1 m high. It has opposing, stalkless, narrow, oblong leaves which are 12 mm long or slightly larger. The leaves are yellow-green in color, with transparent dots throughout the tissue and occasionally with a few black dots on the lower surface. Their flowers measures up to 2.5 cm across, has five petals, and are colored bright yellow with conspicuous black dots. The flowers appear in broad cymes at the ends of the upper branches. The sepals are pointed, with glandular dots in the tissue. There are many stamens, which are united at the base into three bundles.

In addition to its most common use as an antidepressant, *Hypericum* is used as a homeopathic remedy for burns characterized by stinging pain, and is also known to have antibacterial properties.

In accordance with the invention, it has been discovered that a formulation of at least three of the aforementioned ingredients for use in topical application provides highly efficacious and also synergistic effects in the treatments of epidermal burns.

In embodiments of the invention, formulations containing combinations of multiple single remedies are specially selected and formulated to treat a variety of symptom pictures and ailments. Such formulations provide convenience of use by laypersons that are typically unsure of which single remedy to choose for their particular constitution. Such formulations of the invention also treat a wider set of symptoms, and therefore have a broad-based efficacy for groups of ailments, e.g., thermal burns, sunburns, razor burns. The combination of the various single remedies in a multiple component formulation is believed to have an unexpected, synergistic effect such that the efficacy of the combination formulation is greater than the efficacy of any of the single remedies when applied separately.

For example, epidermal burns can occur due to a variety of causes and are characterized by diverse symptoms. A patient could receive a steam or electrical burn characterized by sharp, shooting pain and swelling or sunburn characterized by redness, swelling, peeling and duller pain. Contact burns from curling irons or hot stoves can cause scalding and blistering, leading to an unsightly scar.

The benefit of the present invention is that its work together to address a much broader range of symptoms and types of burns. Embodiments may address the full spectrum of burns from different causes and for different bodily constitutions. Aspects of the invention account for different attendant symptom features including redness, swelling, scraping, scalding, blistering and infection.

It has been discovered that the subject formulation of the invention, when applied shortly after the burn, aids the skin in recovering from the damage caused by epidermal burns. As noted above, this physiological interaction is unique to the subject formulation, and unexpectedly more efficacious when compared with current leading treatment options or individual components of the formulation applied alone.

The subject formulation also provides the following commercial advantages:
1. It is a complete solution in the market for the primary concerns of target audience.
2. It is a simple, easy-to-use product designed for quick application.
3. It is a significantly low cost option to manage epidermal burns, as compared to the multiple steps currently required to achieve the equivalent benefit.

Furthermore, the subject formulation responds to a clearly expressed market need. As stated above, the prevalence of epidermal burns and the inadequacy of current treatment options have been substantiated by market research. A recent survey revealed that 70% of consumers surveyed suffer minor household burns on a regular basis from activities such as cooking, grilling, working in the garage or styling hair. However, 3 out of every 4 consumers surveyed stated they do not currently have an effective solution to care for their burns. The consumers have further stated that the key concerns from an epidermal burn are pain, the risk of infection, and the desire to prevent the appearance of a scar, all of which are effectively addressed by the subject formulation.

Therefore, the subject formulation addresses a real need in the market with a highly efficacious and easy-to-use remedy which can be made available at a lower price and with greater ease of application than a comparable combination of multiple conventional treatments.

It has been determined through various stages of experimentation and evaluation that the inclusion of three or more of the below-mentioned ingredients in the following approximate ranges optimizes the synergistic efficacy of a remedy for epidermal burns, depending on the cause and symptom picture of the burn:
*Cantharis Vesicatoria* 3x: About 2.5 to About 8%
*Calendula Officinalis* Q: About 1 to About 2.5%
*Echinacea Angustifolia* Q: About 1 to About 2.5%
*Hypericum Perforatum* Q/6x: About 2.5 to About 5%

The above ranges are shown as a percentage of the overall product. The total amount of all homeopathic ingredients does not exceed 10% of the overall product formulation. The remaining 90% is comprised of a carrier base which is pharmaceutically compatible for topical application on an epidermal burn.

The use of the above ingredients in combination results in an unexpectedly high level of efficacy. The use of the formulation immediately after the occurrence of an epidermal burn was found to greatly soothe the pain and to remove most, if not all, visible signs of the burn. Even if applied days after experiencing the burn, the formulation was found to be surprisingly efficacious in reducing the appearance of scars and aiding in the recovery of skin integrity, more so than through use of any single ingredient by itself. The improvements in the formula, specifically in the potency and amount of each homeopathic ingredient, were unexpected.

The following examples are further illustrative of specific aspects of the invention. The following examples are based on various stages of experimentation and evaluation, but the present invention is not limited to them.

Example I

The following homeopathic extracts are obtained from commercial sources at the potencies indicated below, and compounded by the procedure outlined below:
*Cantharis Vesicatoria* 3x: About 2.5 to About 8%
*Calendula Officinalis* Q: About 1 to About 2.5%
*Echinacea Angustifolia* Q: About 1 to About 2.5%

A clean, validated reaction vessel suitable for pharmaceutical use (Vessel A) is charged with 775.8 kg Purified Water USP. A mixer is started at 30% to 50% power. Specific ingredients of the carrier base are added as the contents of Vessel A are heated to 50° C., ensuring that the contents are continuously agitated and the temperature is stabilized at 50° C. A separate clean, validated mixing vessel suitable for pharmaceutical use (Vessel B) is prepared, to which added other pharmaceutically acceptable ingredients necessary to create a cream emulsion, which are heated until they are melted. The contents of the two vessels are then combined and gradually cooled under constant mixing, until the temperature is less than 40° C. The homeopathic ingredients are then added to the mixture, which is continuously mixed and agitated while allowing the mixture to cool to room temperature.

The above embodiment of the invention is unexpectedly efficacious in the treatment of first- and second-degree burns with symptoms including pain, redness and blistering, with risk of scarring and infection. It is further found to be unexpectedly efficacious in treating the full range of symptoms above, when applied immediately or soon after experiencing a burn.

Example II

The following homeopathic extracts are obtained from readily available commercial sources at the potencies indicated below, and compounded by the procedure outlined below:

Cantharis Vesicatoria 3×: About 2.5 to About 8%
Calendula Officinalis Q: About 1 to About 2.5%
Echinacea Angustifolia Q: About 1 to About 2.5%

Separately, a gelling agent such as Carbomer, obtained from any readily available commercial source, is dispersed in distilled water and when completely hydrated, is neutralized with sodium hydroxide (20% solution). Once the mixture is uniform, the homeopathic extracts, along with aloe in pharmaceutically acceptable form, are slowly combined.

The above embodiment of the invention is effective in the treatment of sunburns with symptoms including pain, redness, swelling, peeling and soreness, with risk of infection. It is found to be unexpectedly effective in treating the full range of symptoms above, when applied immediately or soon after experiencing sunburn. The gel carrier is particularly effective for application over a larger area of the body, as is typical of sunburns.

Example III

The preferred method of application of the present invention is as follows. As soon as possible upon experiencing an epidermal burn, the subject formulation should be applied to the burn site. It may be spread with a clean finger or with a clean cotton ball or Q-Tip®. The subject formulation, which is white in color, should be rubbed lightly into the affected area until it loses its white color and is visible as a colorless film over the affected area. Upon absorption of the formulation, it should be reapplied as stated above at least 2-3 times or until symptoms disappear.

The following additional Examples illustrate experiments and evaluations which demonstrate the advantages and efficacy of the present invention in the treatment of epidermal burns.

Example IV

The subject of this experiment suffered a first-degree burn on the inside sole of her left foot due to accidental contact with the hot ceramic plate of a flat iron, used to style hair. The burn site was approximately two inches in length and half an inch in width, characterized by stinging pain, redness and swelling. The affected area was also hot to the touch. The subject applied the embodiment of the subject invention described in Example I, above, to the affected area within 1-2 minutes after suffering the burn. The subject perceived an immediate cooling of the affected area and a significant decrease in pain. The subject reapplied the cream within 5-10 minutes after the initial application, and again within 5-10 minutes thereafter. After the second application, a marked decrease in redness or other discoloration was perceived and the pain was minimal. The subject did not reapply after the third application due to a complete disappearance of all symptoms and no visible scar.

Example V

By comparison, another subject suffered a first-degree burn of comparable severity to the burn described in Example V, above, when hot cooking oil splashed on the knuckle of her right index finger. The burn was roughly circular and less than an inch in diameter, and characterized by stinging pain, redness and swelling. Due to habit and proximity to water, the subject washed the affected area within seconds after suffering the burn, and did not apply the subject invention or any other topical treatment to the burn. Although the subject perceived a cooling sensation and slight reduction in pain while her finger was under cold water, the pain and heat immediately returned as soon as the cold water was removed. The pain, redness and swelling persisted for at least 24 hours before slowly dissipating. The burn left a dark brown scar at the burn site which did not visibly fade in the approximately four weeks since the burn.

Example VI

The subject of this experiment suffered a second-degree burn on her right hand due to accidental and sustained contact with a hot liquid. The burn covered the back of the subject's hand from the base of her thumb to the middle joint of her index finger. The burn was characterized by severe stinging pain, significant redness and swelling, and a large blister over most of the affected area. Due to the unavailability of any medicines immediately after suffering the burn, the subject carefully cleaned the burn site and left it open to air. The subject liberally applied the embodiment of the subject invention described in Example I, above, to the affected area 36 to 48 hours after suffering the burn. The subject did not reapply the treatment or any other treatment thereafter. The subject perceived an immediate pain relief as well as cooling of the affected area upon application. Within hours, the blister had disappeared and the redness and swelling were significantly decreased. Almost six months later, there is only a light scar at the burn site.

Example VII

In this example, the subjects, both children under ten years of age, suffered sunburns over large areas of their backs, shoulders, necks and faces, due to overexposure to the sun during a beach vacation. The sunburns were characterized by redness, discomfort and skin irritation. After a few hours, the embodiment of the subject invention described in Example II, above, was liberally applied to the affected areas. The subjects experienced and communicated a sensation of immediate relief from discomfort and irritation from the application of the embodiment of the subject formulation. Within less than an hour after application, the redness was perceived to have fully disappeared.

Example VIII

This experiment is designed to compare the efficacy of the preferred embodiment to that of *Cantharis Vesicatoria* 3× alone, in an embodiment suitable for topical application.

Two subjects are administered a heating element for a duration sufficient to result in a first-degree burn of identical size and severity. Within ten minutes of the burn, one of the embodiments is topically administered to Subject A's affected area, and *Cantharis* is administered to Subject B's affected area. The immediate reactions of Subject A and Subject B are recorded.

It is found in the case of Subject A that there is an immediate cooling sensation of the affected area, and the pain is noticeably reduced. Subject B does not report a cooling sensation or a significant decrease of pain.

The respective creams are reapplied twice more at ten-minute intervals. After one hour, the symptoms of the burns are examined. While it is found in both cases that the pain, redness and swelling of the burn have disappeared, only in the case of Subject A does the formulation also prevent the spread of infection and appearance of a scar.

Example IX

This experiment is designed to compare the efficacy of the various embodiments to that of *Echinacea Angustifolia* Q alone, in an embodiment suitable for topical application.

Two subjects are administered a heating element for a duration sufficient to result in a first-degree burn of identical size and severity. Within ten minutes of the burn, one of the embodiments is topically administered to Subject A's affected area, and *Echinacea* is administered to Subject B's affected area. The immediate reactions of Subject A and Subject B are recorded.

It is found in the case of Subject A that there is an immediate cooling sensation of the affected area, and the pain is noticeably reduced. Subject B does not report a cooling sensation or a significant decrease of pain.

The respective creams are reapplied twice more at ten-minute intervals. After one hour, the symptoms of the burns are examined. It is found in the case of Subject A that all symptoms of the burn have disappeared. Subject B still has pain and other discernible signs of the burn, and the risk of scarring still exists.

The present invention provides methods of manufacturing the present invention in a number of preferred embodiments, as described in the examples above. Further, as demonstrated by the experiments above, the present invention is found to be an excellent treatment for epidermal burns which do not require professional medical treatment. The present invention is found to reduce the duration of symptoms associated with epidermal burns as compared with conventional treatments, as well as to reduce the overall duration of treatment, prevent the risk of infection, and prevent the appearance of scars. The present invention is also found to have a synergistic efficacy greater than that of its individual components, both in terms of duration of treatment and applicability to a wider range of symptoms and causes.

Having thus described the invention the same will become better understood from the following claims in which it is set forth as a non-limiting manner.

What is claimed is:

1. An antipyrotic formulation that is therapeutically effective for treating burns, comprising: a mixture of *Cantharis vesicatoria* in an amount of 2.5 to 8% of the formulation, *Calendula officinalis* in an amount of 1 to 2.5% of the formulation, and *Echinacea angustifolia* in an amount of 1 to 2.5% of the formulation as ingredients; and said ingredients being mixed in a pharmaceutically acceptable carrier suitable for topical application, effective for treating burns upon administration thereof on an epidermal burn, and wherein the combined total amount of said ingredients is less than 10% of the formulation.

2. The formulation of claim 1, further comprising an emulsifier as part of said mixture.

3. The formulation of claim 1, wherein said carrier base comprises petrolatum, with said formulation prepared as an ointment.

4. The formulation of claim 1, wherein said formulation is prepared as a cream emulsion.

5. The formulation of claim 1, wherein said formulation is prepared as a gel.

6. The formulation of claim 1, further comprising aloe.

7. A homeopathic formulation that is therapeutically effective for treating burns, comprising: a mixture of *Cantharis vesicatoria* in an amount of 2.5 to 8% of the formulation, *Calendula officinalis* in an amount of 1 to 2.5% of the formulation and *Echinacea angustifolia* in an amount of 1 to 2.5% of the formulation as ingredients effective for treating first-degree burns upon topical application thereof on a first-degree burn, and wherein the combined total amount of said ingredients is less than 10% of the formulation.

8. The formulation of claim 7, wherein said carrier base comprises petrolatum, with said formulation prepared as an ointment.

9. The formulation of claim 7, wherein said formulation is prepared as a cream emulsion.

10. The formulation of claim 7, wherein said formulation is prepared as a gel.

11. The formulation of claim 7, further comprising aloe.

12. A method for treating burns, comprising administering topically to a burn area of a patient's skin a formulation comprising a mixture of *Cantharis vesicatoria* in an amount of 2.5 to 8% of the formulation, *Calendula officinalis* in an amount of 1 to 2.5% of the formulation, and *Echinacea angustifolia* in an amount of 1 to 2.5% of the formulation as ingredients in a pharmaceutically acceptable carrier suitable for topical application; and said ingredients being mixed in amounts effective for treating burns upon topical application thereof, and wherein the combined total amount of said ingredients is less than 10% of the formulation.

13. The method of claim 12, wherein said carrier is a pharmaceutically acceptable carrier for topical administration.

14. The method of claim 12, further comprising a mixture of C18-22 hydroxyalkyl hydroxypropyl guar, hydrogenated polydecene, isopropyl myristate, lanolin, methylparaben, propylparaben, shea butter, sodium polyacryloyldimethyl taurate, trideceth-10, and purified water.

15. The method of claim 12, wherein said carrier comprises petrolatum, with said formulation prepared as an ointment.

16. The method of claim 12, further comprising a preservative as part of said mixture.

17. The method of claim 12, wherein said formulation is prepared as a cream emulsion.

* * * * *